United States Patent [19]

Evans

[11] 4,327,751
[45] May 4, 1982

[54] HAIR BLEACHING COMPOSITION CONTAINING SOLID POLYOLEFIN POLYMER AND METHOD FOR HAIR BLEACHING

[75] Inventor: Evelyn Evans, Stamford, Conn.

[73] Assignee: Clairol Incorporated, New York, N.Y.

[21] Appl. No.: 118,816

[22] Filed: Feb. 5, 1980

[51] Int. Cl.³ .................... A45D 7/04; A61K 7/135
[52] U.S. Cl. ........................................ 132/7; 424/62; 8/111

[58] Field of Search .............. 132/7; 424/62, 70–71; 8/111

[56] References Cited

U.S. PATENT DOCUMENTS 3,378,444  4/1968  Swanson .......................... 424/62
3,639,574  2/1972  Schmolka ......................... 424/62

Primary Examiner—G. E. McNeill
Attorney, Agent, or Firm—Gabriel P. Katona

[57] ABSTRACT

A composition for lightening hair comprising an alkaline bleaching system and an effective amount of a finely divided solid polyolefin polymer is disclosed.

10 Claims, No Drawings

HAIR BLEACHING COMPOSITION CONTAINING SOLID POLYOLEFIN POLYMER AND METHOD FOR HAIR BLEACHING

The invention herein is concerned with a novel composition for lightening hair, the use of which allows the formulator to control speed at which the lightening effects are achieved. Likewise, it affords the user a greater degree of flexibility in the hair lightening effects obtained. The composition of the present invention is particularly applicable in the field of dimensional hair lightening and hair coloring including hair streaking, frosting, etc.

More specifically, the hair lightening composition of the present invention comprises an alkaline bleaching system and an effective amount of a powdered or finely divided solid inert polyolefin polymer. The incorporation of the powdered polymeric material into the bleaching system functions to control the speed at which the lightening effects on the hair are achieved and, since most bleaching systems are designed to maximize lightening effects, the polymeric material serves, principally, as a lightening decelerator.

With regard to the prior art, it is, of course, well known to bleach hair and reviews of the techniques and bleaching systems used to achieve these effects are readily available. Thus, for example, the subject is discussed in the publication Perfumes, Cosmetics and Soaps, Vol. III Modern Cosmetics, Chapter 7, by W. A. Poucher, revised by George M. Howard, Eighth Edition (1976) (J. Wiley and Sons, New York); and the publication Harry's Cosmeticology, Vol I by R. G. Harry, Sixth Edition (1973) (Leonard Hill Books, London).

Due to the somewhat detrimental effects that the oxidation process in combination with the alkaline condition has upon the hair, most research in this area has been in the area of increasing the speed of the bleaching process and, accordingly, decreasing the application time necessary to achieve the desired degree of lightening. Such research has resulted in the development of numerous types of oxidizing or bleaching agents that may be used alone or in conjunction with various activating agents, i.e., lightening accelerators. For example, U.S. Pat. No. 3,651,209 issued to B. Cohen is concerned with enhancing the bleaching effectiveness of a hydrogen peroxide-persulfate bleaching system by the addition of either an ammonia or an alkali metal peroxydiphosphate. Another field of research in this area has lead to the development of methods of improving the properties of bleached hair to offset partially or completely any impairment of its mechanical properties or appearance caused by the bleaching process and to insure that the bleached hair has a nice feel and luster. Endeavors in this area have lead to the development of a variety of conditioners which may be used with the bleaching system. Thus, for example, U.S. Pat. No. 3,472,604 issued to Dasher et al, discloses the incorporation of a variety of watersoluble polymerizable vinyl monomers containing an acid forming group into a bleaching system. These monomers are then polymerized in situ during the bleaching process. While in this same area, U.S. Pat. No. 4,027,008 issued to Sokol is concerned with the use of various polymeric materials containing amine groups which improve the surface characteristics of the hair when used in conjunction with the bleaching system.

It is known in the art to use powdered products to obtain better control in the application of the bleaching system to the hair and to extend the bleaching time. These powders vary in composition from those which contain absorbent, inert materials, such as magnesium carbonate, magnesium oxide, talc, kaolin, Plaster of Paris, etc. to those powders which themselves provide ammonia and some form of active oxygen when wetted with water or hydrogen peroxide. These powders were at one time called "white henna". The use of such powders are typically beneficial in the process known in the art as retouching. Retouching involves applying the lightening mixture to the root ends of the lightened hair while attempting to minimize contact of the previously lightened hair with the fresh lightening mixture. To be effective, this lightening composition must remain in place at the base of the hair for the time needed for the bleach and retain, while in place, the optimum alkalinity and moisture content needed to continue the bleaching action. Also, it is known in the prior art to use lightening compositions of a gelatinous consistency based upon an inorganic gelling agent as taught in U.S. Pat. No. 3,378,444 issued to Swanson. The use of stable hydrogen peroxide gels based upon polyoxyethylene polyoxypropylene block copolymers in the bleaching of hair, particularly in the area of "frosting", "streaking" and "tipping" has been suggested by Schmolka in U.S. Pat. No. 3,639,574.

Finely divided solid polyolefin polymers, such as polyethylene and polypropylene, are well known in the art and have many commercial uses. Included in the prior art on the utility of these polyolefin polymers are several applications in the field of cosmetics and topical application to the skin. Thus, the Blaustein U.S. Pat. No. 3,196,079 is concerned with a variety of cosmetic or dusting powders based upon a finely divided polyolefin, such as polyethylene and polypropylene, in anhydrous dental preparations, and anhydrous vaginal powder spray formulations. In U.S. Pat. No. 4,164,563 issued to Chang, the use of these finely divided polyolefin polymers is two-fold in the formulation of a non-greasy, occlusive composition for topical application to the skin. Thus, the polymers are used as thickening agents to form a viscous base and are further used as an ointment-forming powder.

In accordance with the present invention, there is provided a novel composition for lightening hair which comprises an alkaline bleaching system and an effective amount of a finely divided solid polyolefin polymer. As discussed above, the polymeric material functions, principally, as a lightening decelerator to decelerate the lightening activity of the standard bleaching system and produce relatively low levels of lightening, as well as, undesirable side effects.

Thus, the subject novel composition overcomes the disadvantages associated with a standard alkaline bleaching system in that it provides a very convenient method for selectively controlling the degree of lightening. Further, it provides a process for lightening hair which limits the level of bleaching and, consequently, the undesirable effects the bleaching process has on the hair. Also, it provides a lightening composition that is more versatile than the presently used lightening compositions.

Exemplary of the versatility of the subject lightening composition is its use in the field of producing dimensional lighting effects. Using prior art bleaching systems, to produce these dimensional effects, the operator or user has to stagger both the time of application of the bleach to the hair and the duration of its application. However, by using the lightening composition of the present invention, the operator or user can apply various strengths of the composition to the hair simultaneously and, subsequently, remove all the mixtures at one time to produce the subtleties and lightening graduations desired. Thus, the use of this lightening composition simplifies the application and decreases the change of lightening errors.

Among the many candidate materials tested as lightening decelerators, the subject polyolefin polymers proved to be unique and ideally suited for this purpose. Thus, they are inert within the environment employed, i.e. not effected by the alkaline, oxidizing reaction conditions. Some "inert" materials tested underwent an undesirable color change under these conditions. The finely divided polymeric material proved to be very compatible with the bleaching system, giving consistencies which can be adjusted to any desired degree. Many of the candidate materials tested had marginal compatibility and gave compositions of undesirable consistency i.e. final consistencies were too thin to be applied to the hair without undesirable dripping. Thus, the subject hair lightening compositions have a consistency which can be adjusted to any desirable degree such that it will have sufficient body and thickness needed for immobility in localized application to the hair and/or scalp (hair roots), and can easily be worked into the hair without dripping or running and then removed after use.

Accordingly, the present invention provides a composition for bleaching or lightening hair at substantially room temperature which includes an alkaline bleaching system, (e.g. an alkaline aqueous solution of hydrogen peroxide, or a compound yielding hydrogen peroxide, or a compound yielding hydrogen peroxide in aqueous media, or an ammonium and/or an alkali metal persulfate, percarbonate, or perborate) and an amount of insoluble, inert finely divided solid polyolefin polymer which is capable of decreasing the bleaching effectiveness, i.e. time and/or ability to achieve maximum bleaching or lightening effect, of the alkaline bleaching system in the absence of the polyolefin polymer.

The present invention also provides for substantially room temperature hair bleaching or lightening compositions based on an alkaline bleaching system in which the body and thickness of the composition is enhanced by incorporation therein of the inert, insoluble finely divided solid polyolefin polymer.

Still further, the present invention provides a novel hair bleaching composition which limits the level of bleaching and damage to that which is necessary to achieve the desired end lightness and which can easily and conveniently be formulated by an operator (beautician) or user into various strengths to selectively control the degree of lightness imparted to the hair.

In another aspect of the present invention provides a method for dimensional hair streaking or coloring (selectively lightening hair, keratin fibers, in a non-uniform way; dimensional effects can duplicate the natural color and highlights achieved by solar exposure, for example). Accordingly, to this method several portions of the lightening/bleaching composition are prepared with each or at least several portions having different amounts of the polyolefin polymer lightening decelerator incorporated therein. The several portions of the lightening composition are applied to selected different portions of the hair and allowed to remain thereon until the desired bleaching effect is obtained. The lightening compositions are then all removed as by washing with water according to conventional practice.

In practicing the method, a standard bleaching system would be chosen based upon its ability to achieve the maximum lightening effect desired. To this standard bleach system, varying amounts of the polyolefin polymers would be added. The polyolefin polymers will effectively decelerate the bleaching activity of the standard bleach system and produce relatively low levels of lightening and damage when applied to the hair for the same treatment time as the standard system. The use of the polyolefin polymer lightening decelerator allows the operator/user to selectively adjust the degree of lightening obtained for a given application time. This in turn allows the operator/user to apply various bleach strengths to the hair simultaneously and subsequently remove all the mixtures at one time to produce the subtleties and lightening graduations desired.

The quantity of the finely divided polyolefin polymer contained in the subject hair lightening composition will vary depending upon the particular use for which the composition is designed and depending upon the particular bleaching system employed. Generally, it has been found that from about 11% to about 28% by weight based upon the total weight of the composition of the finely divided polyolefin polymeric material is effective. A preferred range is from about 21.5% to about 23.5% by weight based upon the total weight of the lightening composition.

The terminology of "an alkaline bleaching system" as used herein and in the appended claims is used in its art accepted meaning to define that portion of the composition which comprises the oxidizing or bleaching agent, water, alkalizing agents or buffers, organic solvents, thickening agents, antioxidants or stabilizers, sequestering agents, perfumes, dyes, surfactants, conditioners, etc.

While the exact composition of the alkaline bleaching system will vary depending upon its specific end use, an essential component of the bleaching system is the oxidizing or bleaching agent. The specific kind of oxidizing agent employed will depend upon the use to which the hair lightening composition is designed. Useful oxidizing agents for compositions of this invention include hydrogen peroxide, urea peroxide, melamine peroxide, sodium perborate, sodium percarbonate and sodium persulfate. The preferred oxidizing agent is hydrogen peroxide.

The quantity of oxidizing agent used will vary according to the particular agent employed and the specific end use of the composition. Generally, the oxidizing agent will be present in the range from about 0.5% to about 20% by weight based upon the total weight of the bleaching system.

When hydrogen peroxide is employed as the oxidizing agent, the preferred range is from about 2% to about 4% by weight, based upon the total weight of the bleaching system.

The bleaching system component of the subject lightening composition is an aqueous based composition with the terminology being used in its usual generic sense as inclusive of any water-containing compositions embodied in the invention. Thus, this includes true solutions or mixtures of materials dissolved or dispersed in the aqueous medium. The amount of water present in this component can vary over a wide range depending in a large measure on the quantity of the other ingredients.

The pH of the bleaching system will, of course, be on the basic side within the range of from about 8 to about 11, with the preferred range of from about 9 to about 10. Any of a wide variety of alkalizing agents or buffers may be used to maintain the pH within the desired range. Ammonium hydroxide, because of its freedom from toxicity over a wide concentration range and its economy is a widely used alkalizing agent. Other compatible ammonia derivatives may be used as the alkalizing agent, for example, an alkylamine such as ethylamine; or an alkanolamine, such as monoethanolamine, diethanolamine, and aminomethylpropanol. Likewise, any of the common inorganic alkalizing agents may be used, such as sodium or potassium hydroxide, sodium or potassium carbonate, sodium phosphate, sodium hydrogen phosphate, sodium silicate and the like.

Various organic solvents may also be present in the bleaching system for the purpose of solubilizing any of the components which may be insufficiently soluble in water. Generally, the solvent selected is such as to be miscible with water and innocuous to the skin. Suitable solvents include, for example, ethanol, isopropanol, glycerine, ethylene glycol, propylene glycol, ethylene glycol monoethyl ether, diethylene glycol, diethylene glycol monoethyl ether, etc.

Various thickening agents may also be incorporated in the bleaching system component of the subject composition. Useful thickening agents including sodium alginate, gum arabic, cellulose derivatives, such as methyl cellulose, hydroxyethyl cellulose, etc. Likewise, inorganic thickening agents such as bentonite, talc and kaolin are useful.

The bleaching system component may have an antioxidant incorporated in it, and useful antioxidants for this purpose include sodium sulphite, thioglycollic acid, sodium hydrosulfite, and ascorbic acid. Sequestering agents may also be present in the bleaching system. Useful sequestering agents include ethylenediamine tetraacetic acid and its various sodium salts, tetrasodium pyrophosphate and the like. Surfactants, additionally, may be present in the bleaching system and useful surfactants include the anionic, non-ionic and cationic type. Also, the bleaching system may contain dyes, perfumes, and conditioners as are conventionally employed in the art.

A large number of alkaline bleaching systems are known in the prior art and these are useful as this component of the subject lightening composition. More detailed information on the bleaching system is available from the above cited references by Poucher and by Harry, as well as the above discussed patents.

The polyolefin polymers useful in the subject hair lightening compositions have from 2 to about 6 carbon atoms in the recurring unit and, generally, will have a molecular weight in the range of about 3,000 to about 150,000. Thus, representative examples of useful polyolefins include polyethylene, polypropylene, the polybutylenes, the polypentenes, and the polyhexenes. Preferably, the polyolefin polymer is selected from the group consisting of polyethylene and polypropylene and the preferred polyolefin is polyethylene. The polyolefin polymers may be prepared in accordance with a variety of polymerization processes known in the art and are commercially available. Further information concerning the preparation and properties of these polymers may be found in Encyclopedia of Polymer Science and Technology, H. Mark, ED.(John Wiley and Sons, Inc., New York), Vol. 6 (1967) and Vol. 11 (1969); and other standard reference works in this field.

Any suitable method known in the art for pulverization may be used to prepare the finely divided polymeric material of the subject composition. These methods include, for example, micropulverization and cryogenic pulverization and the like. The useful particle size for the polyolefin material of the subject composition is in the range of from about 44$\mu$ to about 177$\mu$, with a preferred range of from about 64$\mu$ to about 100$\mu$. The useful mesh size as determined in accordance with U.S. Standard Sieve size is in the range of from about 60 to about 80. The shape of the particles may be of the conventional shape or special shapes, such as spherical.

The preferred polymeric material for the subject composition is based upon polyethylene having a molecular weight in the range of from about 3000 to about 4000, or polypropylene having a molecular weight in the range of from about 3400 to about 3600. Suitable finely divided polyethylene and polypropylene are available commercially from several sources. Thus, useful polyethylenes include the AC-POLYETHYLENES (Allied Chemical Company, Morristown, New Jersey) such as 6A, 8A, 9A, 9F, 617A, 6AF, 8AF and 9AF; the MICROTHENES (U.S.I. Chemical Company, Kingsport, Tennessee) such as C-14. Useful polypropylenes include those of the HERCOFLAT series (Hercules, Inc. Wilmington, Delaware). Additional information concerning these finely divided polymers is readily available in the prior art, such as the above discussed patents, i.e. U.S. Pat. Nos. 3,196,079; 3,878,138; 3,936,402; and 4,164,563.

EXAMPLE 1

Sodium metasilicate (5.07 groms) was coated with 5.5 grams of a finely divided silica (Cab-O-Sil M5) by shaking in a suitable container. Aluminum distearate (3.0 grams) was mixed with 0.1 grams of dye. All of the above ingredients were added to a blender along with 35.07 grams of potassium persulfate, 12.0 grams of sodium stearate, 1.2 grams of the disodium salt of ethylenediamine tetraacetic acid, 2.2 grams of sodium lauryl sulfate (Duponol C), 8.03 grams of ammonium persulfate, 3.0 grams of hydroxypropyl methylcellulose (Methocel 60HG), 2.0 grams of ammonium vinylacrylic acid (Carbopol 962) and 22.83 grams of finely divided polyethylene (AC—POLYETHYLENE 9F). The resulting mixture was mixed in the blender with a bar for about 5 minutes and the blending continued without a bar for about 15 minutes. At the end of this period, the product was sieved through a 20 mesh sieve. Fifty grams of the sieved product was mixed with 4 ounces of a 6% aqueous hydrogen peroxide solution and applied to the hair for a period of one hour at ambient temperatures.

EXAMPLE 2

When the mixture of Example 1 is prepared using finely divided polypropylene in place of polyethylene, similar results are obtained.

EXAMPLE 3

| Material | Composition A<br>% by Wt. |
| --- | --- |
| Cab-O-Sil M5 | 8.505 |

-continued

| Composition A | |
|---|---|
| Material | % by Wt. |
| Sodium metasilicate | 6.750 |
| Potassium persulfate | 35.57 |
| Sodium stearate | 12.00 |
| Aluminum distearate | 3.00 |
| Disodium EDTA | 1.20 |
| Duponol C | 1.20 |
| Ammonium persulfate | 10.76 |
| Methocel 60HG | 3.0 |
| Carbopol 962 | 2.00 |
| A-C Polyethylene Grade 617A | 16.015 |

50 grams of Composition A above were mixed with 4 ounces of 6% aqueous hydrogen peroxide solution. This mixture is applied to hair for a period of one hour at ambient temperatures.

EXAMPLE 4

| Material | % by Wt. |
|---|---|
| Cab-O-Sil M5 | 5.5000 |
| Sodium metasilicate | 5.0700 |
| Potassium persulfate | 35.0950 |
| Sodium stearate | 12.0000 |
| Aluminum distearate | 3.0000 |
| Disodium EDTA | 1.2000 |
| Duponol C | 2.2000 |
| Ammonium persulfate | 8.0300 |
| Methocel 60 HG | 3.0000 |
| Carbopol 962 | 2.0000 |
| A-C Polyethylene 9A | 22.8300 |
| Dye | 0.0750 |
| | 100.0000 |

50 grams of the above composition are mixed with 4 ounces of 6% aqueous hydrogen peroxide and then applied to the hair for a period of one hour at ambient temperatures.

| | % by Wt. | |
|---|---|---|
| Material | Ex. 5 | Ex. 6 |
| Cab-O-Sil M5 | 5.50 | 5.50 |
| Sodium metasilicate | 6.76 | 5.07 |
| Potassium persulfate | 35.07 | 35.07 |
| Sodium stearate | 12.00 | 12.00 |
| Aluminum distearate | 3.00 | 3.00 |
| Disodium EDTA | 1.20 | 1.20 |
| Sodium lauryl sulfate | 2.20 | 2.20 |
| Ammonium persulfate | 10.70 | 8.03 |
| Methocel 60HG | 3.00 | 3.00 |
| Carbopol 962 | 2.00 | 2.00 |
| A-C Polyethylene 9F | 18.57 | 22.93 |

50 grams of each of the above compositions (Example 5 and Example 6) were mixed with 4 ounces of 6% aqueous peroxide and applied to the hair for 60 minutes at 38° C. A bleach comparison showed that the bleaching obtained with composition of Example 6 is darker than that obtained with the composition of Example 5.

Although the invention has been described with reference to specific forms thereof, it will be understood that many changes and modifications may be made without departing from the spirit of this invention.

What is claimed is:

1. A composition for lightening hair comprising an alkaline bleaching system and an effective amount of a finely divided solid polyolefin polymer.

2. The composition of claim 1 wherein the finely divided solid polyolefin polymer is a member selected from the group consisting of polyethylene and polypropylene.

3. The composition of claim 2 wherein the polyolefin polymer is polyethylene.

4. The composition of claim 2 wherein the polyolefin polymer is polypropylene.

5. The composition of claim 1 wherein the particle size of the polyolefin polymer is in the range of from about 64$\mu$ to about 100$\mu$.

6. The composition of claim 1 wherein the alkaline bleaching system is based upon a peroxide oxidizing agent.

7. The composition of claim 3 wherein the particle size of the polyethylene is in the range of about 64$\mu$ to about 100$\mu$.

8. The composition of claim 4 wherein the particle size of the propylene is in the range of from about 64$\mu$ to about 100$\mu$.

9. The composition of claim 1 wherein the finely divided solid polyolefin polymer is present in an amount of from about 21.5% to about 23.5% by weight.

10. A method for dimensional hair streaking which comprises the steps of:
(1) forming several portions of a lightening composition, each portion of the lightening composition comprising an alkaline bleaching system and an effective amount of a finely divided solid polyolefin polymer wherein the effective amount in at least one portion differs from the effective amount in at least one other portion;
(2) applying each of the several portions of the lightening compositions to different portions of the hair; and
(3) removing the several portions of the lightening compositions from the hair.

* * * * *